(12) United States Patent
Wesselmann et al.

(10) Patent No.: US 9,095,687 B2
(45) Date of Patent: Aug. 4, 2015

(54) CATHETER, SYSTEM FOR INSERTING AN INTRALUMINAL ENDOPROSTHESIS AND METHOD FOR MANUFACTURING SAME

(75) Inventors: Matthias Wesselmann, Glattfelden (CH); Markus Angst, Zurich (CH)

(73) Assignee: BIOTRONIK VI Patent AG, Baar (CH)

( * ) Notice: Subject to any disclaimer, the term of this patent is extended or adjusted under 35 U.S.C. 154(b) by 1220 days.

(21) Appl. No.: 12/370,829

(22) Filed: Feb. 13, 2009

(65) Prior Publication Data
US 2009/0204082 A1   Aug. 13, 2009

(30) Foreign Application Priority Data
Feb. 13, 2008   (DE) .......................... 10 2008 008 925

(51) Int. Cl.
*A61F 2/06*      (2013.01)
*A61M 25/10*   (2013.01)

(52) U.S. Cl.
CPC ........... *A61M 25/10* (2013.01); *A61M 25/1029* (2013.01); *A61M 25/1038* (2013.01); *A61M 2025/1031* (2013.01)

(58) Field of Classification Search
CPC .............. A61F 2/958; A61M 25/1038; A61M 2025/1004; A61M 25/1002; A61M 25/10; A61M 25/104
USPC ................. 623/1.11; 606/191, 192, 194, 198; 604/96.01, 103.06–103.09, 916
See application file for complete search history.

(56) References Cited

U.S. PATENT DOCUMENTS

| | | | |
|---|---|---|---|
| 5,041,125 A | | 8/1991 | Montano, Jr. |
| 5,456,666 A | | 10/1995 | Campbell et al. |
| 5,458,572 A | * | 10/1995 | Campbell et al. ........ 604/103.08 |
| 5,853,389 A | * | 12/1998 | Hijlkema ................. 604/103.07 |
| 6,013,055 A | * | 1/2000 | Bampos et al. .......... 604/103.07 |
| 2003/0055378 A1 | * | 3/2003 | Wang et al. .............. 604/103.07 |
| 2003/0130716 A1 | * | 7/2003 | Weber et al. ................. 623/1.11 |
| 2005/0177130 A1 | * | 8/2005 | Konstantino et al. ......... 604/509 |

(Continued)

FOREIGN PATENT DOCUMENTS

| | | |
|---|---|---|
| DE | 69119753 T2 | 1/1997 |
| DE | 69531784 T2 | 4/2004 |

(Continued)

OTHER PUBLICATIONS

Search Report for German Patent Application No. 10 2008 008 925.7; Nov. 3, 2008.
Search Report for European Patent Application No. 09150824.2; Jul. 6, 2009.

*Primary Examiner* — Katherine M Shi
(74) *Attorney, Agent, or Firm* — Greer, Burns & Crain, Ltd.

(57) ABSTRACT

A catheter having a balloon (10) which has at least one wing (12) in the undilated state, the balloon having at least one fold element (11, 11', 31, 32, 41, 42) running essentially in the longitudinal direction for each wing (12), such that in folding the balloon (10), the fold element is arranged in an area of the wing (12) with a minimum in the bending radius, said area running in the longitudinal direction. Also disclosed is a system for introducing an intraluminal endoprosthesis, preferably a stent, into a body cavity consisting of an intraluminal endoprosthesis and a catheter having the balloon as described. Further, disclosed are methods of producing such a catheter and such a system.

35 Claims, 13 Drawing Sheets

(56) References Cited

U.S. PATENT DOCUMENTS

| | | | |
|---|---|---|---|
| 2005/0250672 A9 * | 11/2005 | Speck et al. | 514/1 |
| 2006/0015133 A1 * | 1/2006 | Grayzel et al. | 606/192 |
| 2006/0182873 A1 | 8/2006 | Klisch et al. | |
| 2007/0129748 A1 | 6/2007 | Eidenschink et al. | |
| 2007/0244501 A1 | 10/2007 | Horn et al. | |
| 2007/0260300 A1 * | 11/2007 | Gregorich et al. | 623/1.11 |
| 2008/0114294 A1 * | 5/2008 | Holman et al. | 604/96.01 |
| 2009/0054837 A1 * | 2/2009 | Von Holst et al. | 604/103.08 |
| 2009/0105800 A1 * | 4/2009 | Sabaria | 623/1.11 |

FOREIGN PATENT DOCUMENTS

| | | |
|---|---|---|
| DE | 69832811 T2 | 8/2006 |
| EP | 0414350 A1 | 2/1991 |
| EP | 1738791 A1 | 1/2007 |
| WO | 0185229 A2 | 11/2001 |
| WO | 03049603 A2 | 6/2003 |
| WO | 2007055732 A1 | 5/2007 |

\* cited by examiner

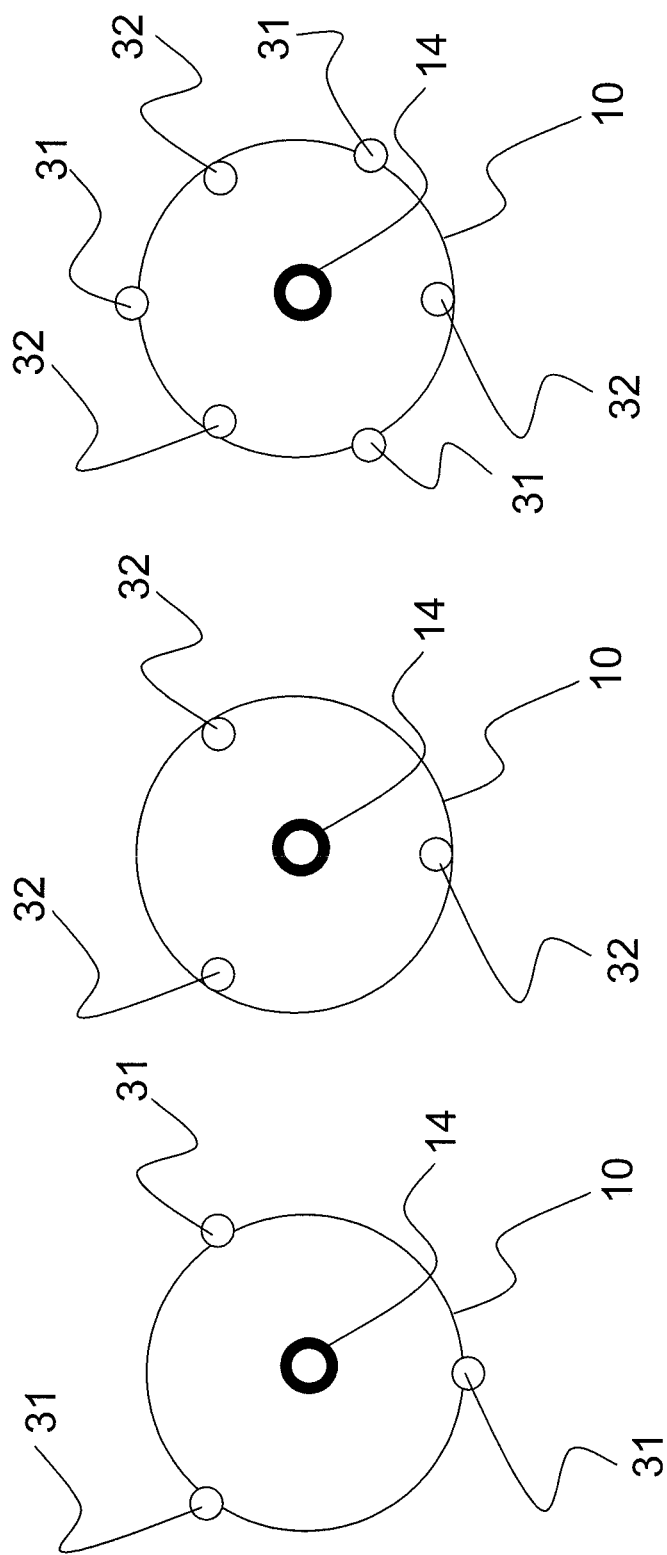

CATHETER, SYSTEM FOR INSERTING AN INTRALUMINAL ENDOPROSTHESIS AND METHOD FOR MANUFACTURING SAME

PRIORITY CLAIM

This patent application claims priority to German Patent Application No. 10 2008 008 925.7, filed Feb. 13, 2008, the disclosure of which is incorporated herein by reference in its entirety.

FIELD

The present disclosure relates to a catheter with a balloon, whereby the balloon has at least one wing in an undilated state. The present disclosure also relates to a system for introducing an intraluminal endoprosthesis, preferably a stent, into a body cavity, comprising the intraluminal endoprosthesis and a catheter having a balloon which has at least one wing in an undilated state. The present disclosure further relates to a method for manufacturing such a catheter and a method for manufacturing such a system.

BACKGROUND

Catheters are tubes or tubing of various diameters that can be inserted into the respective body cavity to be treated. So-called balloon catheters, which are used mainly in angioplasty to dilate or reopen a vessel, have a guide wire that is first inserted into the vessel to be treated. Then a tube which has an undilated folded balloon in a predefined area of the tube, is advanced along the guide wire up to the site of the blood vessel to be treated so that the balloon is placed in the area of the site of the blood vessel to be treated, e.g., where there is a stenosis. Then the balloon is dilated, i.e., unfolded and expanded, so that the site to be treated is reopened or dilated and the flow of body fluid through the blood vessel is no longer hindered or is not hindered to the previous extent. Finally, the balloon is deflated and removed from the blood vessel along the guide wire. At the same time or thereafter, the guide wire is also retracted out of the blood vessel.

For insertion of balloon catheters, the balloon must first be introduced in a folded, i.e., undilated state, into the body cavity to be treated. With the balloon catheters currently in use, the balloons are folded after being shaped and then are secured by applying compressive forces (referred to as impressing) to the folded balloon. The steps required to do so as well as the corresponding device are complex because high temperatures and long impressing times are required in the impressing step. Furthermore, the heat treatment often results in shrinkage of a balloon, thereby altering the dimensions of the balloon. Another disadvantage of this procedure is that the wing shape is lost after the initial dilatation i.e., the balloon is refolded in a defective manner to some extent or is folded inconsistent with its pre-inflation configuration. This is due to the fact that a fold produced in the traditional way stores very little energy on inflation of the balloon so that the refolding tendency in deflation is low. On retraction of a defectively refolded balloon, an increased pull-back force is required. Likewise, an increased force is required to redilate a stent, to reach a side branch through a stent segment or to pass through a second stenosis.

With traditional catheters, the balloon has wings which run parallel to the axis of the balloon. These balloons create an anisotropic bending moment of the folded balloon. The disadvantage of such folding is that the catheter in the area of the balloon is more susceptible to kinking of the catheter and the wings stand up in tight curves on insertion into the body cavity to be treated so that insertion is prevented. After deflation, wings running parallel to the axis of the catheter may also cause unwanted transverse folding when the inside shaft expands with the balloon in a non-plastic manner. This also requires an increased pull-back force.

Furthermore, balloons that are integrally furnished with an active pharmaceutical substance may release residues of the substance to the surrounding body fluid at the wrong point in time, e.g., during retraction in the event of uncontrolled refolding. This may cause adverse effects.

For purposes of the present disclosure, the term "active pharmaceutical substance" (also known as "active therapeutic substance") means an active ingredient (medication) of plant, animal or synthetic origin or a hormone which is used in a suitable dosage as a therapeutic agent to influence conditions or functions of the body, as a substitute for active ingredients, such as insulin, that are synthesized naturally by the human or animal body and to eliminate disease pathogens, tumors, cancer cells or exogenous substances or to render them harmless. The release of the substance in the environment of the endoprosthesis has a positive effect on the course of healing or counteracts pathological changes in the tissue due to the surgical procedure and/or serves to render malignant cells harmless in oncology.

Such active pharmaceutical substances have an anti-inflammatory and/or antiproliferative and/or spasmolytic effect, so that, for example, restenoses, inflammations or (vascular) spasms can be prevented. In certain exemplary embodiments, such substances may consist of one or more substances from the group of active ingredients consisting of calcium channel blockers, lipid regulators (such as fibrates), immunosuppressants, calcineurin inhibitors (such as tacrolimus), the antiphlogistics (such as cortisone or diclofenac), anti-inflammatories (such as imidazoles), antiallergics, oligonucleotides (such as dODN), estrogens (such as genistein), endothelializing agents (such as fibrin), steroids, proteins, hormones, insulins, cytostatics, peptides, vasodilators (such as sartans) and substances with an antiproliferative action, such as taxols or taxans, in this case, preferably paclitaxel or sirolimus.

German Patent No. 691 19 753 describes a balloon catheter having a catheter body and a balloon arranged along the length of the catheter body. The balloon is also provided with a device for its inflation and deflation from the outside and a device for supplying a medication or a combination of medications for treatment or diagnosis within a hollow organ of a body when the catheter is positioned in the hollow organ and inflated. The supply device has microcapsules on the outside of the balloon where the microcapsules are secured in folds on the balloon such as those formed when the balloon is shrunk. The microcapsules here are designed so that the microcapsules can be ruptured or degraded. The microcapsules open when they remain on the walls of the hollow organ. The capsules may also rupture due to the application of ultrasonic waves.

The disadvantage of the catheter described in German Patent No. 691 19 753 is that microencapsulated medications must be used to implement the dispensing of medications, but microencapsulated medications are expensive and complicated to produce. Furthermore, microencapsulation is not possible for all medications that may be considered. Additionally, a balloon of such a catheter provided with microcapsules has a comparatively large diameter whose profile cannot be used in practice and which makes the catheter rigid and inflexible. Furthermore, the medication can be rubbed off not only at the site to be treated but also on insertion or dilatation of the balloon. This increases the side effects associated with the treatment.

Balloon catheters may also be used to introduce intraluminal endoprostheses to a site to be treated in a body cavity.

Intraluminal endoprostheses in the form of stents are currently widely used because they allow a simple and inexpensive treatment. These stents often have a tubular or hollow cylindrical basic mesh which is open on both longitudinal ends. The basic mesh of such an endoprosthesis is inserted by means of a catheter into the hollow cavity to be treated and is then dilated or released. After removal of the catheter, the endoprosthesis serves to support the body cavity. Such stents have become established, in particular, for treatment of vascular diseases. Through the use of stents, constricted areas in the vessels can be dilated so that the vascular lumen is enlarged.

Intraluminal endoprostheses are often provided with active pharmaceutical substances which are released in the body over a certain period of time.

These active pharmaceutical substances may serve, for example, to prevent restenoses or agglomerations. Due to the release of active pharmaceutical substances with which such intraluminal endoprostheses are provided, it is possible to perform merely a local treatment, i.e., elution of an active ingredient essentially only in the tissue surrounding the intraluminal endoprosthesis. This process is also known as local drug delivery ("LDD"). The treatment site where the active ingredient should manifest its pharmacological effect is thus directly adjacent to the site of implantation of the intraluminal endoprosthesis.

Intraluminal endoprostheses that consist of a material which is subject to biodegradation are currently also in use. For purposes of the present disclosure, biodegradation means hydrolytic, enzymatic or other metabolic degradation processes in a living organism caused mainly by the body fluids coming in contact with the endoprosthesis and leading to a gradual dissolution of at least large portions of the endoprosthesis. The term "biocorrosion" is often synonymous with the term biodegradation. For purposes of the present disclosure, the term "bioabsorption" includes the subsequent absorption of the degradation products by the living organism. Such biodegradable materials may consist of polymers or metals. The abbreviation AMS (absorbable metal stent) is also often used in conjunction with stents. Such stents contain a biodegradable metal, preferably magnesium and/or a magnesium alloy. Other degradable metals that may be used include iron, zinc, tungsten and alloys thereof.

In intraluminal endoprostheses consisting of a biodegradable material and provided with an active pharmaceutical substance, the problem often arises that the active pharmaceutical substances do not adhere properly to the basic mesh of the endoprosthesis or do not function in the desired manner because, in the biodegradation of the endoprosthesis, the pH of the environment may change and/or the endoprosthesis may undergo uncontrolled corrosion and thereby undergo a high degree of penetration. Release of the active pharmaceutical substance thus does not take place in the desired manner or within the desired time frame.

SUMMARY

The present disclosure describes several exemplary embodiments of the present invention.

One aspect of the present disclosure provides a catheter, comprising: a balloon having a dilated and an undilated state and having at least one wing in the undilated state which has at least one fold element running essentially in the longitudinal direction for each wing, such that when the balloon is folded, the fold element is arranged in an area of the wing running in the longitudinal direction with a minimum in the bending radius.

Another aspect of the present disclosure provides a system for introducing an intraluminal endoprosthesis, such as a stent, into a body cavity, the system comprising a) an intraluminal endoprosthesis and b) a catheter comprising a balloon having a dilated and an undilated state and having at least one wing in the undilated state which has at least one fold element running essentially in the longitudinal direction for each wing, such that when the balloon is folded, the fold element is arranged in an area of the wing running in the longitudinal direction with a minimum in the bending radius, wherein the intraluminal endoprosthesis is fixedly arranged on the folded balloon such that the intraluminal endoprosthesis at least partially surrounds the folded balloon.

A further aspect of the present disclosure provides a method for producing a catheter, comprising a) providing a balloon having a dilated and an undilated state and having at least one wing in the undilated state which has at least one fold element running essentially in the longitudinal direction for each wing, such that when the balloon is folded, the fold element is arranged in an area of the wing running in the longitudinal direction with a minimum in the bending radius; b) providing a catheter base body having an inside shaft and an outside shaft; and c) connecting the balloon to the inside shaft and the outside shaft.

An additional aspect of the present disclosure provides a method for producing a system for introducing an intraluminal endoprosthesis, such as a stent, into a body cavity, the method comprising a) providing an intraluminal endoprosthesis; b) providing a catheter comprising (i) a balloon having a dilated and an undilated state and having at least one wing in the undilated state which has at least one fold element running essentially in the longitudinal direction for each wing, such that when the balloon is folded, the fold element is arranged in an area of the wing running in the longitudinal direction with a minimum in the bending radius, and (ii) a base body having an inside shaft and an outside shaft; c) forming at least one wing on the balloon; d) bringing the at least one wing into close contact with the inside shaft; and, e) fixedly associating the intraluminal endoprosthesis on the folded balloon such that the intraluminal endoprosthesis at least partially surrounds the folded balloon.

Yet another aspect of the present disclosure provides a balloon for use in a catheter, the balloon having a dilated and an undilated state and comprising: at least one wing in the undilated state which has at least one fold element running essentially in the longitudinal direction for each wing, such that when the balloon is folded the fold element is arranged in an area of the wing running in the longitudinal direction with a minimum in the bending radius.

One aspect of the present disclosure provides a catheter that can be folded more easily and avoids, in particular, the above-noted problems of the catheter during refolding. Another aspect of the present disclosure provides a system for a catheter and an intraluminal endoprosthesis which additionally limits the release of the active pharmaceutical substance on introduction of the intraluminal endoprosthesis to the site where the intraluminal endoprosthesis is used.

A further aspect of the present disclosure provides a method for manufacturing a catheter and a system that is simple and inexpensive.

This aspect is achieved by a catheter for which the balloon material comprises at least one fold element running essentially in the longitudinal direction for each wing, such that when the balloon is folded, the fold element is arranged in an area of the wing running in the longitudinal direction where the bending radius is at a minimum.

For purposes of the present disclosure, the term "longitudinal direction" means the direction of the axis of the catheter. For purposes of the present disclosure, the term "fold element running essentially in the longitudinal direction" means a fold element that runs primarily in the longitudinal direction, i.e., also obliquely or in a spiral in the longitudinal direction, so the fold element can run with one component in a direction perpendicular to the longitudinal direction. Folds or fold lines are areas of the balloon membrane in which the bending radius is at a minimum. These folds are formed when the balloon membrane is overstretched on the outside (on the outer wing end) or on the inside (at the connection point of neighboring wings). For purposes of the present disclosure, the term "fold" used in conjunction with "folds of the balloon" means the initial folding of the balloon at the time of manufacture of the catheter as well as the refolding (referred to as re-wrapping) in deflation.

The balloon of the present disclosure having the at least one fold element has an advantage that the balloon is folded along the at least one fold element so that the predetermined and desired arrangement of the wings on the balloon is facilitated. In particular, the balloon collapses on refolding and with further folding of the balloon repeatedly along the at least one fold element so that the refolding (referred to as rewrapping) is reproducible. This prevents defective refolding and increased pull-back forces.

It is especially preferable if the at least one fold element has an altered stiffness, preferably a lower stiffness, in comparison with the other areas of the balloon. This facilitates folding along the running direction of the fold element because the balloon membrane always folds along the weakest area as soon as the balloon is deflated.

A preferred option for integrating differences in stiffness into the balloon membrane consists of the balloon having recesses or elevations or at least a sudden change in wall thickness in the area of the at least one fold element.

As an alternative or in addition to the possibilities described hereinabove for integrating fold elements, preferably differences in stiffness, into the balloon, there is also the advantageous possibility that the at least one fold element will develop an area of the balloon having a different material composition from the other areas of the balloon. These areas (running with the greatest extent in the longitudinal direction of the balloon and having a square, circular, ellipsoidal or rectangular cross section, for example) are designed to be web-shaped, for example, whereby such a web may be provided on the surface of the balloon or embedded in the volume of the balloon. For example, with a balloon material made of PEBAX® (polyether block amide), areas with the material PA12 running in the longitudinal direction on the outside along the balloon can be introduced, these areas being under greater tensile stress in folding than is the balloon material. In folding the balloon, these areas are thus arranged in the minimum bending radius areas, where one wing of a balloon is adjacent to the neighboring wing. Conversely, when using PA12 as the balloon material, areas of the material PEBAX running on the inside along the balloon in the longitudinal direction can be introduced. These areas are arranged at the tip of a wing in folding the balloon because these areas are under less tensile stress than the remaining balloon material. The two exemplary embodiments may also be combined. Other combinations of materials may also utilize the materials PA11 and PVC. In another exemplary embodiment in which the aforementioned materials may also be used, the material of the balloon not belonging to the fold elements is provided with a reinforcing layer thereby creating regions of increased wall thickness. The reinforcing layer may be embedded in the material of the balloon as an intermediate layer.

In another exemplary embodiment, the at least one fold element, which is preferably designed as a recess or as an elevation, has interruptions that ensure a greater stability of the fold lines.

A catheter in which the at least one fold element runs at a fixedly predefined angle to the balloon axis is also preferred. This also means that the respective wing is created at an angle to the balloon axis. The at least one fold element here runs around the balloon in or on the surface of the balloon and does not run merely parallel to the axis of the balloon. In this way, a uniform bending moment of the folded balloon about its longitudinal axis is created. In the case of bending of the system applied from the outside, the tensile forces and compressions largely cancel one another while strains and stretching compensate for one another. The catheter of the present disclosure has a uniform trackability because the bending moment of the folded balloon is independent of the angle. Furthermore, the peripheral wings no longer stand up in tight curves because the prevailing forces are compensated, as described hereinabove, and the stiff wings no longer stand perpendicular to the direction of stress and thus can better dissipate deformations on their flanks.

In another exemplary embodiment of an catheter of the present disclosure, the fold elements of the balloon are formed by longitudinal struts, which form a structure that is arranged on the inside and/or on the outside of the balloon and supports the balloon at defined locations. In addition, depending on the choice of the structure materials, very high stresses in folding the balloon can be absorbed by the structure. The longitudinal struts may also run in a spiral. Nitinol, for example, or thermoplastics may be used as the structure materials.

In one exemplary embodiment that is also preferred, the catheter in the undilated state has at least one active pharmaceutical substance which is arranged at least partially under the at least one wing of the balloon of the catheter.

For purposes of the present disclosure, the "undilated state" includes all states of the balloon of the catheter in which the balloon is not completely unfolded, i.e., at least one wing is still at least partially present on the balloon even if it is already partially expanded. Likewise, states in which the balloon is deflated are also included, i.e., the balloon has already been dilated once and was then collapsed again. However, the term "undilated state" addresses, in particular, states in which, after folding and impressing, the balloon is in a completely folded form and/or is again almost completely folded after being deflated.

For purposes of the present disclosure, the term "arranged under the at least one wing of the balloon" also means that the at least one active pharmaceutical substance is arranged inside the wing of the balloon, i.e., in or on the surfaces of the wing, which are arranged one over the other after folding. The active pharmaceutical substance arranged under the wing is thus covered by the part of the respective wing which is on the outside.

With the arrangement of an active pharmaceutical substance under the at least one wing, it is preferable if the at least one active pharmaceutical substance is provided on one or more carriers which are arranged beneath one or more wings of the balloon. In this way, it is possible in a particularly simple manner to use a catheter that has already been used once for dispensing an active pharmaceutical substance because one or more carriers may easily be arranged beneath the one or more wings.

It is also especially preferred if the wings of the balloon are adhesively bonded by means of the at least one active pharmaceutical substance. This reinforces the effect that the active pharmaceutical substance does not escape from the wings in an uncontrolled manner. However, the adhesive bond is of a type such that the adhesive bond is ruptured on dilatation of the balloon so that the balloon can be dilated without any significant delay and without exerting any great force.

The catheter can be manufactured especially inexpensively if the at least one active pharmaceutical substance, preferably containing taxols and/or taxans, especially preferably paclitaxel or sirolimus and/or preferably containing at least one hyperplastic active ingredient with a distribution coefficient between the distribution coefficients of butanol and water of ≥0.5 is applied to the balloon by immersion, spraying, painting or pressing, optionally embedded in a vehicle or carrier. The hyperplastic active ingredient optionally contained in the active pharmaceutical substance here serves to allow locally limited treatment of potentially hyperproliferative tissue. For example, a cytostatic, a corticosteroid, a prostacycline, an antioxidant, an agent for inhibition of cell proliferation or an immunosuppressant may be used as the active antihyperplastic agent.

The exemplary embodiments disclosed hereinabove are also achieved by a system in which the intraluminal endoprosthesis is arranged securely on the folded balloon in the catheter disclosed hereinabove, such that the intraluminal endoprosthesis at least partially surrounds the balloon.

The statement that the endoprosthesis at least partially surrounds the folded balloon expresses the fact that the endoprosthesis is arranged on the surfaces of the balloon that face outward after folding. The endoprosthesis at least partially covers these outside surfaces. The arrangement of the endoprosthesis on a balloon is not to be regarded as permanent. At the start of balloon dilatation, the endoprosthesis is arranged fixedly on the balloon, i.e., even in storage and insertion into the human or animal body. After achieving the maximally dilated state, when the balloon is deflated, the endoprosthesis remains in the body cavity while the catheter is removed from the body cavity.

Using the system disclosed hereinabove, the active pharmaceutical substance which is not necessarily present in a microencapsulated form is released to the surrounding body fluid and to the tissue directly at the site where the intraluminal endoprosthesis is implanted in the body cavity because only through dilatation is the active pharmaceutical substance released through opening of the wings. Furthermore, due to the fixed arrangement of the intraluminal endoprosthesis on the balloon, it is guaranteed that the system of intraluminal prosthesis and balloon will assume a very small volume on the whole on insertion of the system into the body cavity so that the system can be handled in a flexible and simple manner. Furthermore, it is not necessary for the active pharmaceutical substance to be provided in a microencapsulated form. In addition, the release of the at least one active pharmaceutical substance may take place immediately after dilatation of the balloon together with the intraluminal endoprosthesis because of the absence of microencapsulation, thus yielding a rapid onset of effect of the active pharmaceutical substance and an effect exactly at the site of treatment.

In an especially preferred exemplary embodiment, the intraluminal endoprosthesis, used in conjunction with the system of the present disclosure, is crimped onto the balloon. This is a very simple and inexpensive method of attaching the intraluminal endoprosthesis to the balloon.

Furthermore, it is advantageous if the intraluminal endoprosthesis is designed as a biodegradable stent, preferably as an AMS stent. After fulfilling its treatment function, such a stent is no longer present in the tissue of the treated body cavity (the stent dissolves almost completely) and thus the stent causes fewer adverse effects. Since the active pharmaceutical substance is released to the environment only during the short dilatation time of the balloon of the catheter, the degradation of the biodegradable endoprosthesis has very little or no influence on the effect of the active pharmaceutical substances because, at this point in time, the degradation has not yet begun or has started only to an insignificant extent.

Especially good coverage of the balloon provided with the active pharmaceutical substance in the undilated state is achieved in a preferred exemplary embodiment when the intraluminal endoprosthesis completely covers the outer surfaces of the folded balloon beneath the endoprosthesis. For purposes of the present disclosure, the term "outer surfaces" means the outside surfaces or surface areas of the folded balloon which are on the outside after folding and impressing. The outside surfaces or surface areas of the balloon arranged one above the other beneath the wing or wings do not belong to these outer surfaces.

In an especially preferred exemplary embodiment, the intraluminal endoprosthesis is provided luminally with an easily detachable coating, preferably with one or more substances from the group consisting of sugars, preferably polysaccharides, glycans, glucose, glycogen, amylose, amylopectin, chitin, callose and cellulose, and fats, preferably cholesterin, cholesterol, palm oil, partially hydrogenated soy oils and saturated oils. After implantation, such a layer is easily washed away by body fluid so that no residues of the active ingredient remain on the luminal side of the intraluminal endoprosthesis and, therefore, endothelialization is not hindered.

The exemplary embodiments disclosed hereinabove are also achieved by a method for manufacturing a catheter in which the balloon is first provided with at least one fold element, after which the catheter base body having an inside shaft and an outside shaft is provided, and then the balloon is connected to the inside shaft and the outside shaft. The catheter base body here has an inside shaft and an outside shaft, with the outside shaft surrounding the inside shaft. The balloon is connected at one end to the inside shaft and at the other end to the outside shaft. If necessary, markings are provided on the inside shaft in the area of the balloon to serve as X-ray markers, for example. The method for manufacturing a catheter herein disclosed can be implemented easily and is inexpensive in implementation.

In another exemplary embodiment, the balloon may also be connected first without a fold element to the catheter base body that is provided, in which case the balloon is connected at one end to the inside shaft and at the other end to the outside shaft. Next the at least one fold element, which is created by means of chemical methods, for example, is inserted into the balloon.

In both exemplary methods, the balloon is folded and impressed according to the folds of the balloon as specified in manufacturing the catheter.

An exemplary manufacturing method for a catheter of the present disclosure includes manufacturing the balloon by blow molding before connecting the balloon to the catheter base body, where the blow mold is provided with a recess or elevation or with multiple recesses or elevations, e.g., in the form of round or elongated nubs or interrupted grooves in the area where the at least one fold element should be formed. Alternatively, the balloon may be manufactured by injection blow molding, where at least one defined sudden change in wall thickness is created in the area of the at least one fold element. Through the recesses and elevations in the blow mold as well as the at least one sudden change in wall thickness in injection blow molding, differences in stiffness are created in the balloon in a simple manner leading to the development of the at least one fold element.

As explained hereinabove, it is also advantageous to provide the balloon with a Self-X (self-expanding) structure consisting of longitudinal struts on the outside and/or inside, supporting the balloon in certain areas. The supporting structure may be manufactured from a highly elastic material, which must always be in contact with the inside wall of the balloon even in the maximally dilated state (at the rated burst pressure). If the balloon internal pressure is lowered, then the balloon is kept open only in the area of the supporting structure and collapses in the unsupported areas between the longitudinal struts. The course of the folds can thus be controlled very accurately. Such a structure could consist of two spiral Nitinol wires, for example, which are welded to rings in the balloon necks.

The at least one fold element may also be created advantageously such that the balloon is treated locally by a thermal method, e.g., by means of a laser and/or by means of a solvent in the area of the at least one fold element, preferably before applying the at least one active pharmaceutical substance. Furthermore, the balloon may also be provided with an additional reinforcing material outside of the at least one fold element, likewise preferably before applying the at least one active pharmaceutical substance.

As explained above, it is advantageous if the at least one fold element is provided so that it runs in or on the surface of the balloon at a fixedly predefined angle to the balloon axis.

In a preferred exemplary embodiment of the manufacturing process, before folding the balloon, first at least its active pharmaceutical substance is applied to or into the outer surface of the balloon of the catheter, preferably by means of immersion, spraying, painting or pressing. Such a method supplies an active pharmaceutical substance in or on the balloon surface for direct treatment of the body cavity into which the catheter is inserted and does so in an especially simple and inexpensive manner.

The active pharmaceutical substance is preferably embedded in a carrier on the balloon where optionally a contrast medium and/or an organic salt and/or an inorganic salt and/or at least one other additive may be provided in the carrier, if necessary, the added substance serving, for example, to improve the mechanical adhesion to the balloon surface and/ or to improve the release of the active pharmaceutical substance to the vascular wall and/or to improve the absorbency of the vascular wall. The active substance preferably contains taxols and/or taxans, especially preferably paclitaxel or sirolimus and/or preferably at least one hyperplastic active ingredient with a distribution coefficient between those of butanol and water of ≥0.5. These additives improve the properties of the carrier with the active pharmaceutical substance.

In addition, in a preferred exemplary embodiment of the catheter manufacturing method, the excess at least one active pharmaceutical substance on the outer surface or surfaces of the balloon on the outside after folding is removed after the folding step, preferably by wiping the pharmaceutical substance away. This ensures that the at least one active pharmaceutical substance is arranged only beneath the wing. To wipe away the active pharmaceutical substance, a porous paper towel, a sponge or the like, optionally impregnated with a solvent, may be used.

It has also proven especially advantageous that the at least one active pharmaceutical substance is cured or polymerized before arranging the intraluminal endoprosthesis on the balloon. Curing may also be accomplished with the help of a polymer or a solvent on the balloon surface. Then the active pharmaceutical substance adheres especially well to the surface of the balloon. The curing or polymerization is especially accomplished by UV radiation, radiation with beta rays and or a thermal treatment.

The at least one active pharmaceutical substance is preferably applied together with a vehicle or carrier (e.g., a polymer and/or a solvent). In the case of use of a solvent, the solvent evaporates during and/or after application. Expelling the solvent while at the same time hardening the polymer carrier is also known as curing. Solvents that may be used preferably include the following substances, depending on the active pharmaceutical substance: DMSO, acetone, ether (diethyl ether), methanol, isopropanol, esters and other suitable alcohols. When using polymers or a polymer-like substance as the carrier and curing aid, attention must be paid to the fact that the polymers or polymer-like substance is readily soluble or releases the medication rapidly. From this standpoint, hyaluronic acid, P4HB, polyvinylpyrolidone, liposomes, nanoparticles, silk proteins and cyclodextrins are especially suitable. As an additional component of the carrier to which the active pharmaceutical substance is applied, contrast media and/or organic salts and/or inorganic salts as well as other solid additives may be provided. These serve to improve the mechanical adhesion to the surface of the balloon and/or to improve the release of the active pharmaceutical substance to the vascular wall and/or to improve the uptake ability of the vascular wall for the active pharmaceutical substance.

When using a carrier for the active pharmaceutical substance, which contains a solvent to be expelled, the method of the present disclosure is preferably modified such that after applying the carrier with the solvent and active pharmaceutical substance, the balloon is folded and the excess material on the outside after application is removed. Next the balloon is inflated (dilated) and the solvent is expelled, e.g., by heat treatment. Then the active pharmaceutical substance, optionally containing other additives in the carrier as described hereinabove, is arranged fixedly on the surface of the balloon. Next the balloon can be folded again and the active pharmaceutical substance is arranged beneath the wings of the balloon, where the balloon is folded for this purpose by using a balloon of the present disclosure that folds as defined hereinabove at the same locations as the first fold, so that the at least one active pharmaceutical substance is reliably situated beneath the wings.

To improve the uniformity of the applied active pharmaceutical substance, then in an advantageous exemplary embodiment of the method, the active pharmaceutical substance is applied to the balloon when the balloon is in the inflated (dilated) state.

In another preferred exemplary embodiment of a production process for a balloon, the inside shaft and the outside shaft of the catheter are rotated and/or shifted relative to one another where the balloon is already connected to the inside shaft and the outside shaft before rotating and/or shifting. The rotated and/or displaced state in this exemplary embodiment is the normal state of the instrument. In dilatation, the inside shaft and the outside shaft store the torsion energy and thus facilitate the spiral refolding of the balloon in deflation.

Finally, another exemplary embodiment is achieved by a system consisting of a catheter with a balloon and an intraluminal endoprosthesis, where first the catheter is produced by one of the methods described hereinabove, then at least one wing is formed on a balloon, next this at least one wing is applied closely to the inside shaft and then the intraluminal endoprosthesis is fixedly arranged on the folded balloon in such a way that the endoprosthesis at least partially surrounds the balloon.

The production process for the system is inexpensive and easy to perform and yields a system that allows the desired local treatment of the body cavity.

The production process is further simplified when the intraluminal endoprosthesis is arranged on the balloon by crimping.

In a preferred exemplary embodiment, the distal and proximal ends of the balloon are excluded when applying at least one active pharmaceutical substance, preferably by covering the ends during the application. Uncontrolled release of the at least one active pharmaceutical substance out of the areas of the proximal or distal end of the balloon which might not be surrounded completely by the endoprosthesis is thereby prevented.

As already explained hereinabove, it is advantageous if, before arranging the intraluminal endoprosthesis on the balloon, the intraluminal endoprosthesis is provided luminally with a coating that is easily washed off and the coating is luminal, preferably with one or more of the substances from the group consisting of sugars, preferably polysaccharides, glycans, glucose, glycogen, amylose, amylopectin, chitin, callose and cellulose, and fats, preferably cholesterin, cholesterol, palm oil, partially hydrogenated soy oils and saturated oils.

BRIEF DESCRIPTION OF THE DRAWINGS

Various aspects of the present disclosure are described hereinbelow with reference to the accompanying figures.

Additional goals, features, advantages and possible applications of the present disclosure are derived from the following description of exemplary embodiments on the basis of the figures. All the features described and/or illustrated graphically here, either alone or in any combination, constitute the subject matter of the present disclosure, even independently of how they are combined in the individual claims or their reference back to previous claims.

FIGS. 8a, b and c show cross-sectional views of three other exemplary embodiments of a catheter of the present disclosure, each with at least one Self-X structure with the balloon dilated;

DETAILED DESCRIPTION

Figure 1:
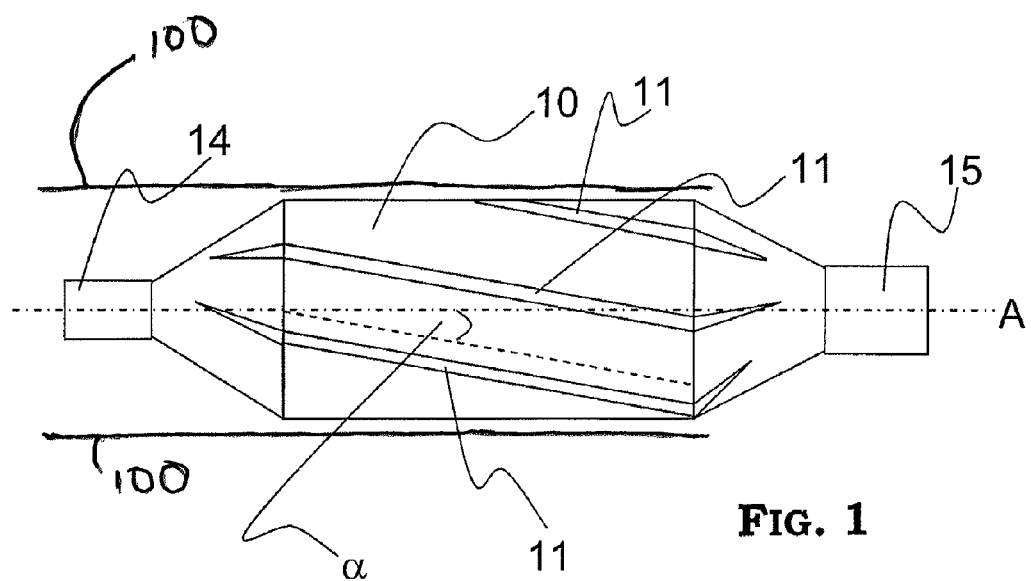
FIG. 1 shows a side elevational view of a first exemplary embodiment of a catheter of the present disclosure, where the balloon is shown in the dilated state.

The first exemplary embodiment of a catheter of the present disclosure illustrated in FIG. 1 shows the balloon 10 of the catheter in the dilated state (without pressure). The balloon 10 has several fold elements (hereinafter also called "fold lines") 11 which run parallel over most of their length and form an angle .alpha. to the catheter axis A (.alpha.noteq.0.degree.) on the surface of the balloon 10. The fold lines 11 extend essentially along the longitudinal direction embodied by the catheter axis A. Each fold line 11 is embodied as a recess with a certain width in the balloon membrane. As an alternative exemplary embodiment, the fold line 11 may also be embodied as an elevation with a certain width or jump in wall thickness and/or change in wall thickness. This gives the balloon 10 a greater stiffness in the area of the fold line 11 than in the other areas of the balloon. On the front distal end, the balloon 10 is connected to the inside shaft 14, while at the rear proximal end, the balloon 10 is attached to the outside shaft 15. The balloon 10 is preferably welded to the inside shaft 14 and/or outside shaft 15. Also shown is an intraluminal endoprosthesis 100 as described hereinabove at least partially surrounding the balloon 10.

In the area of its distal and proximal ends, the fold lines 11 do not run in parallel and develop gradually into the adjacent area of the balloon 10. This means that in the case of a fold line 11 designed as a recess, for example, its depth decreases gradually in the area of its ends until the fold line 11 assumes a depth of zero. At the same time, the width of the fold lines 11 decreases in the area of their ends.

The width and height of the elevations and/or recesses depend on the diameter of the balloon 10, the balloon material used and the wall thickness of the balloon membrane. The width of the elevations or recesses is at least twice as great as the wall thickness of the balloon membrane. The balloon membrane is preferably thermoformed so that the grooves do not detract from the original wall thickness of the balloon but instead the contour changes (comparable to that of corrugated sheeting).

Figure 2A:
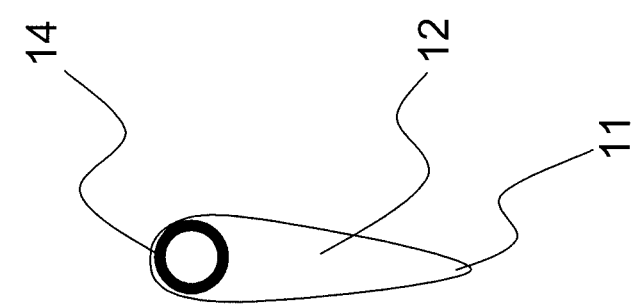
FIGS. 2a, b and c show side cross-sectional views of second, third and fourth exemplary embodiments of a catheter of the present disclosure with one, two and three wings in the folded state.
Figure 2B:
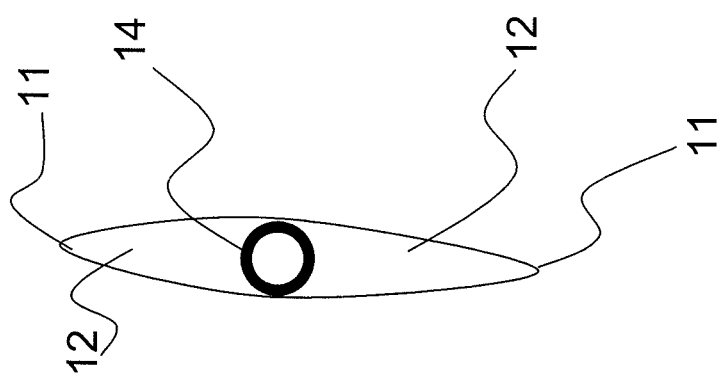
Figure 2C:
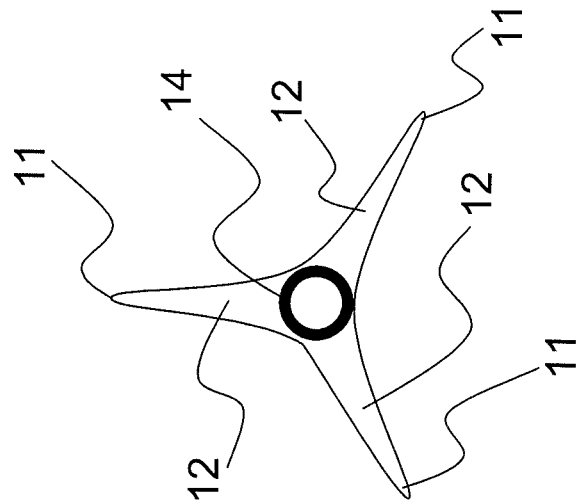

In the cross sections of the first exemplary embodiment shown in FIGS. 2a, b and c, it can be seen that the fold lines 11 are each arranged on the front end of the wing 12 and thus each is in the area with the smallest bending radius. A minimum in the bending radius of the wings 12 occurs approximately where the forward distal end of the wings 12 is arranged, i.e., the wing 12 is folded along the fold line 11. Alternatively or additionally, a fold line may be provided where the one wing 12 is adjacent to the other wing, as in second, third and fourth exemplary embodiments in FIGS. 2b and c with two and/or three wings 12. In FIGS. 2a, b and c, the inside shaft 14 of the catheter which is on the inside is also surrounded by the balloon 10.

Figure 3C:
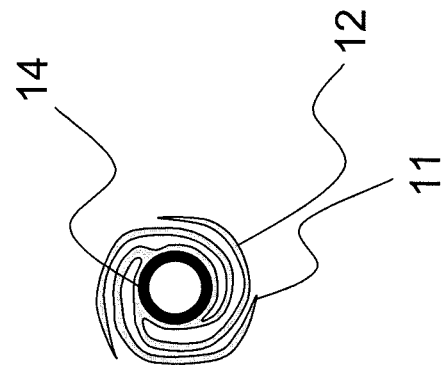
FIGS. 3a, b and c show side cross-sectional views of the exemplary embodiments of FIGS. 2a, b and c in the state in which the wings are in close contact with the inside shaft.
Figure 3B:
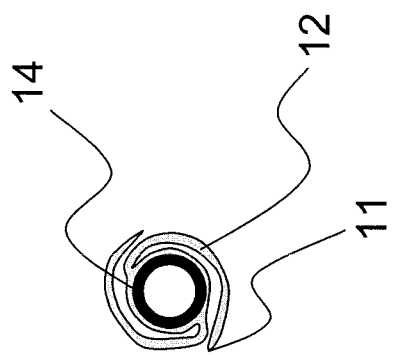
Figure 3A:
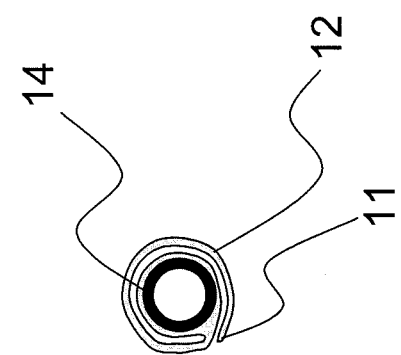

In FIGS. 3a, b and c, the catheter of FIGS. 2a, b and c is shown again in the state in which the wings 12 are in close contact with the inside shaft 14. This is achieved by the fact that the wings 12 are wrapped around the inside shaft and are impressed in this position.

Figure 4:
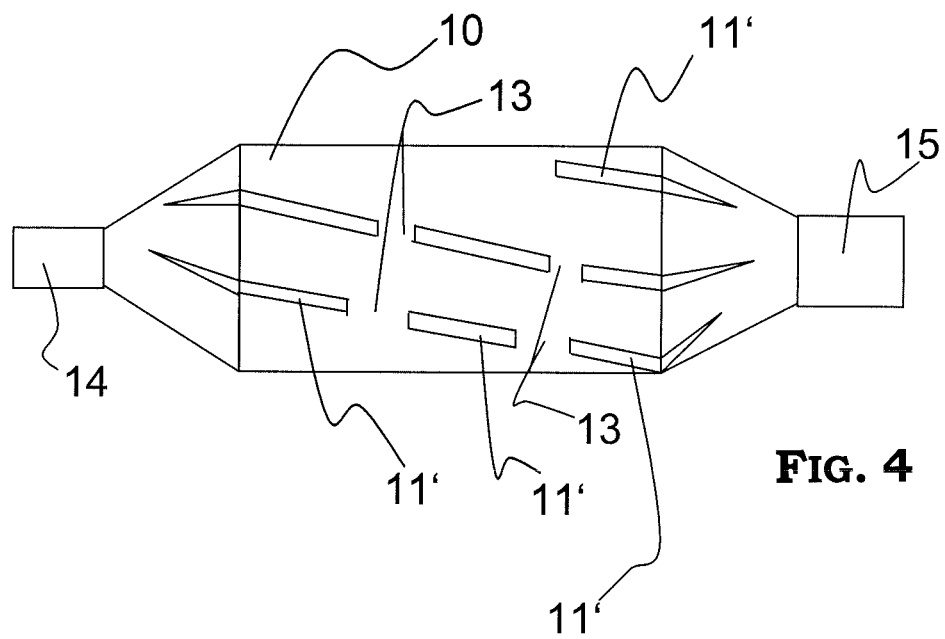
FIG. 4 shows a side elevational view of a fifth exemplary embodiment of a catheter of the present disclosure with the balloon open or dilated (without pressure), where the balloon has interrupted peripheral recesses.

The fifth exemplary embodiment of the catheter shown in FIG. 4 has fold elements or fold lines 11' in the form of recesses where multiple interruptions 13 are provided over their entire length (i.e., in the longitudinal direction). It is also conceivable for only one interruption 13 to be provided along a fold line 11'.

Figure 5:
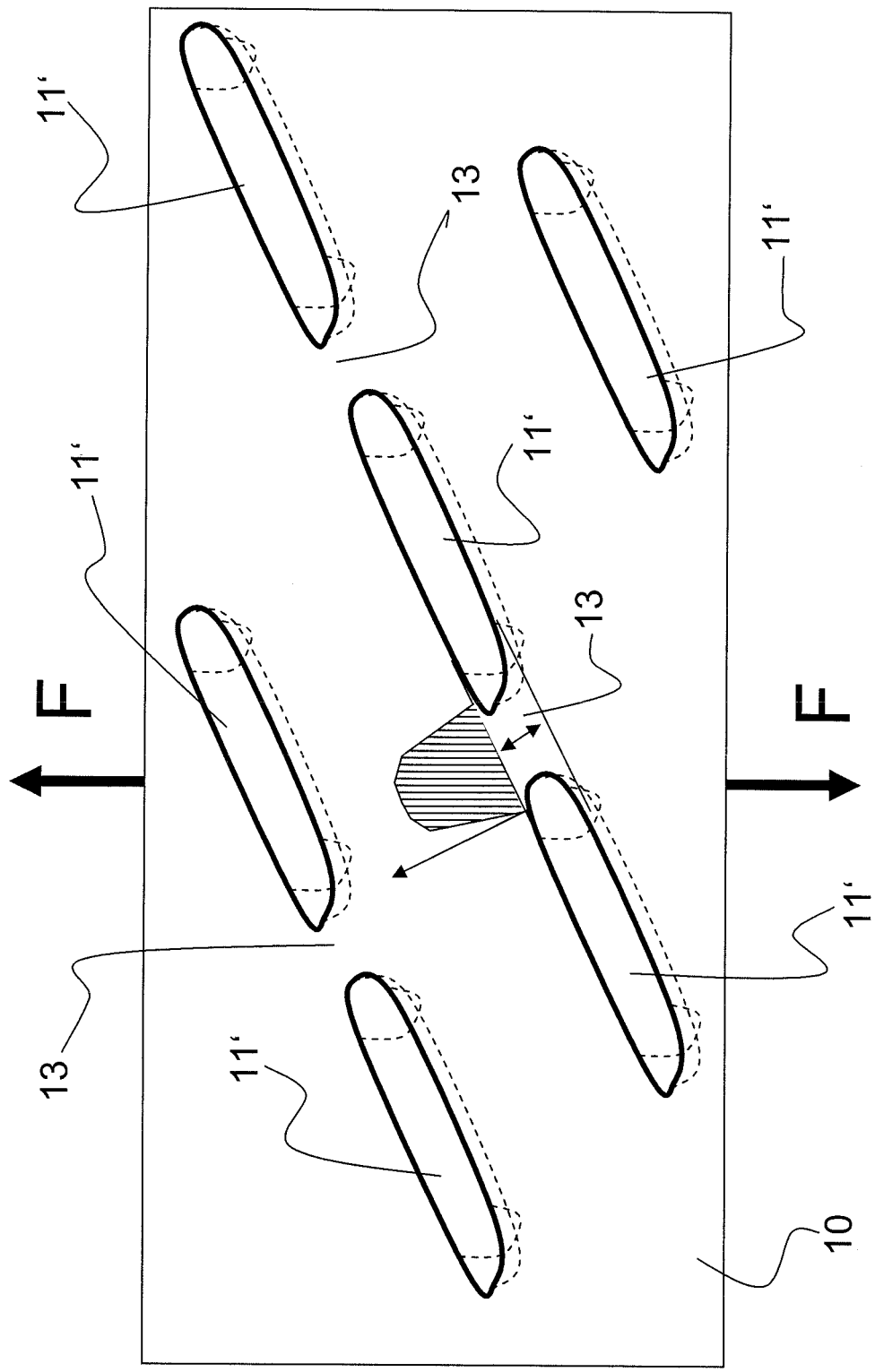
FIG. 5 shows an enlarged detail of the balloon surface of the fifth exemplary embodiment shown in FIG. 4.

In the detail of the balloon 10 shown in FIG. 5, it can be seen that a locally increased tensile load (represented as a hatched area) occurs with tensile forces F in the area (interruptions, webs) 13 between the recesses along the fold lines 11' embodied as recesses. In this way, the recesses along the fold lines 11' are realigned when the balloon is deflated so that development of folds along the fold lines 11' is supported.

Figure 6:
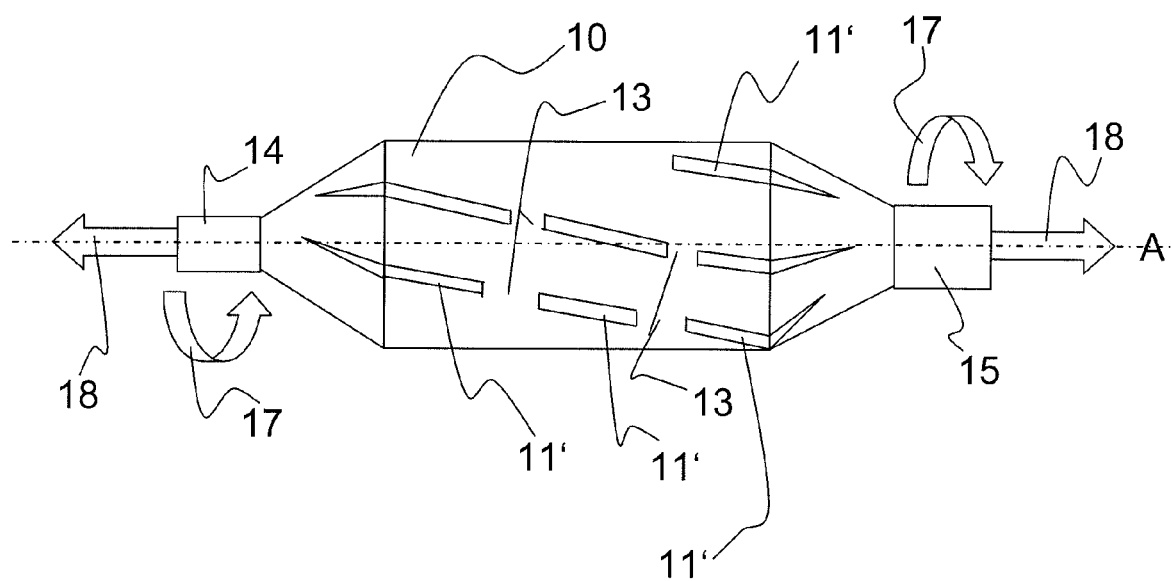
FIG. 6 shows a side elevational view of the fifth exemplary embodiment of FIG. 4 during the production of same in a view from the side with the balloon open or dilated.

Finally, the production of the exemplary embodiment illustrated in FIGS. 4 and 5 is shown in FIG. 6. After attaching the balloon 10 to the inside shaft 14 and to the outside shaft 15, the inside shaft 14 and outside shaft 15 are rotated relative to one another (twisted, as shown by directional arrows 17). In addition, the inside shaft 14 and outside shaft 15 are moved away from one another in the direction of the longitudinal axis A (shifted, cf. arrow 18). The inside shaft 14 and outside shaft 15 are thus rotated and shifted and attached to one another. Such a balloon 10, which is mounted on the catheter so that the balloon is twisted and shifted in the basic state, exerts a torsional force on the catheter in dilatation. This torsional force is stored in the inside shaft 14 and in the outside shaft 15 and acts on the balloon ends in deflation. Such a balloon 10 can be folded back more effectively along the fold lines 11' with the peripheral fold lines 11'.

Figure 7:
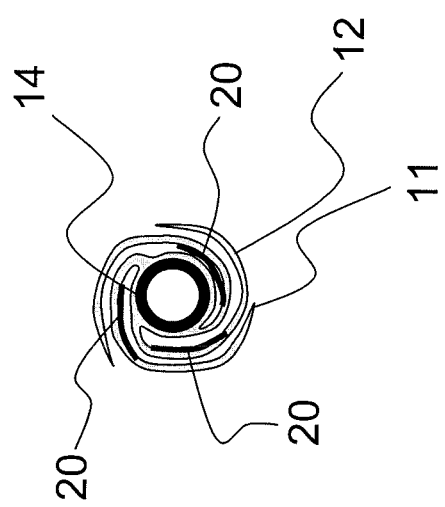
FIG. 7 shows a cross-sectional view of a sixth exemplary embodiment of a catheter of the present disclosure with three wings and an active pharmaceutical substance.

FIG. 7 shows a sixth exemplary embodiment of an inventive catheter in which an active pharmaceutical substance 20 is arranged beneath each wing 12. This active pharmaceutical substance 20 is preferably arranged in or on a carrier that adheres fixedly to the balloon surface which comes to lie in the wing interspaces.

It should be pointed out that FIGS. 3a, b and c as well as FIG. 7 contain schematic diagrams inasmuch as parts of the wing 12 are shown as elevated with respect to the respective wing 12 in comparison with the reality of the other areas. With the real folding of the balloon 10, the balloon areas of each wing 12 arranged on the inside in the direction of the inside shaft 14 are in close contact with the areas of the wing 12 underneath so that on insertion and extraction of the catheter only minor forces (including pull-back forces) need be applied.

Figures 9A, 9B, 9C:
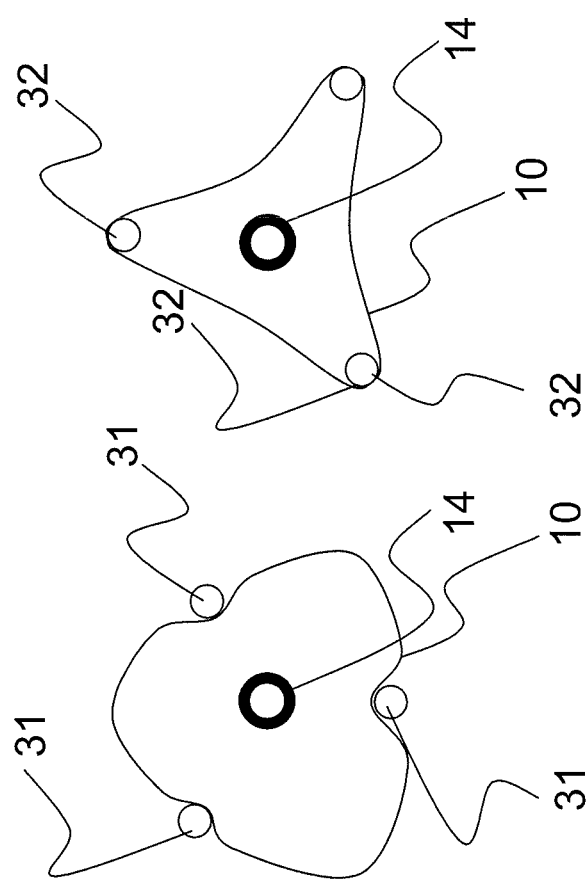
FIGS. 9a, b and c show cross-sectional views of the exemplary embodiments shown in FIG. 8 in a partially deflated state.

FIG. 8 shows additional exemplary embodiments of an inventive catheter where a Self-X structure is provided. In the exemplary embodiment shown in FIG. 8a, the Self-X structure has longitudinal struts 31 as fold elements running on the outer surface of the balloon 10 in the longitudinal direction. The catheter shown in FIG. 8b has longitudinal struts 32 as fold elements on the inside surface of the balloon. In the exemplary embodiment shown in FIG. 8c, longitudinal struts 31 and/or 32 are provided on the outer surface of the balloon as well as on the inner surface of the balloon. FIGS. 9a, b and c show the behavior of the balloon membrane in deflation of the catheter exemplary embodiments shown in FIGS. 8a, b and c. The longitudinal struts 31 arranged on the outer surface of the balloon in FIGS. 8a, 9a and/or 8c, 9c relax because the longitudinal struts 31 move with the balloon membrane beneath them in the direction of the inside shaft 14. On the other hand, the longitudinal struts 32 arranged on the inner balloon surface retain their position (cf. FIGS. 9b and 9c). Due to this movement of the balloon membrane caused by the Self-X structure, the balloon forms the corresponding number of wings 12 (see FIG. 10), where the longitudinal struts 31 are arranged at the minimum of the bending radius in the area of the transition between two wings 12, and the longitudinal struts 32 are arranged at the minimum of the bending radius on the front ends of the wings 12.

Figure 10C:
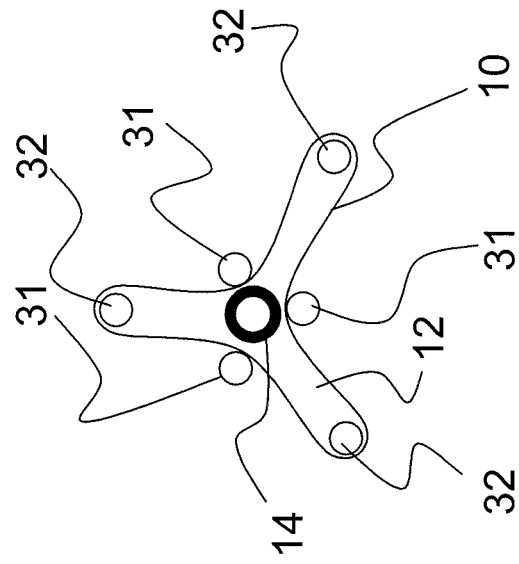
FIGS. 10a, b and c show cross-sectional views of the exemplary embodiments shown in FIGS. 8a, b and c in a further deflated state in comparison with FIGS. 9a, b and c.
Figure 10B:
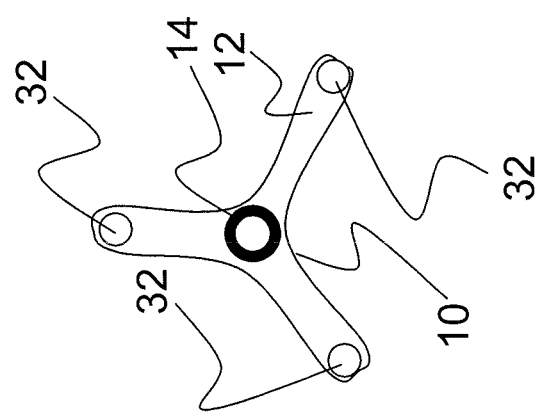
Figure 10A:
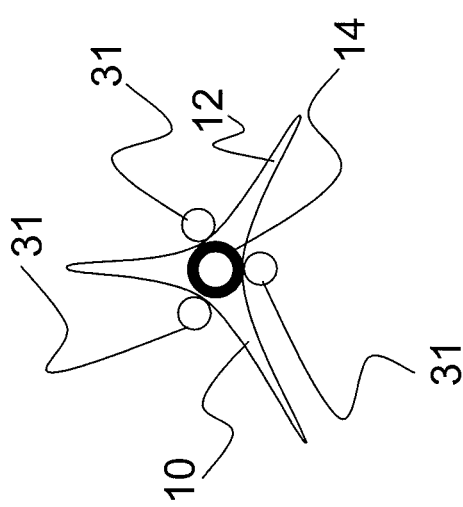

With regard to FIGS. 8, 9 and 10, it should be pointed out that the subfigures a, b and c of the FIGS. 8, 9 and 10 each represent an exemplary embodiment of a catheter of the present disclosure in different stages of deflation, e.g., FIGS. 8a, 9a and 10a show the same exemplary embodiments in different stages of deflation. The same thing is also true of the exemplary embodiments shown in FIGS. 11, 12 and 13.

Figure 11C:
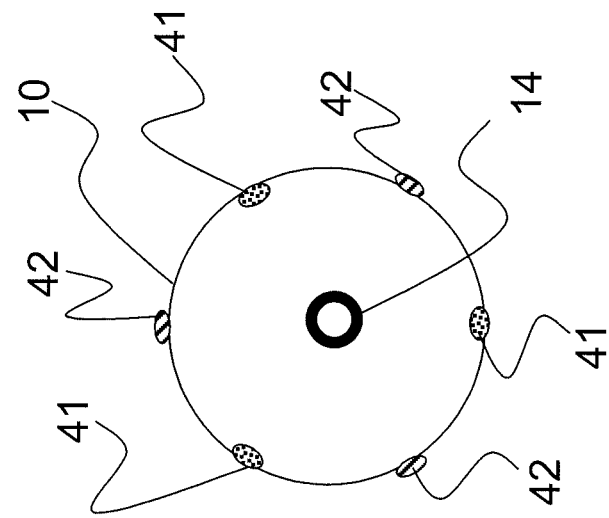
FIGS. 11a, b and c show cross-sectional views of three other exemplary embodiments of a catheter of the present disclosure with different materials in or on the balloon surface with the dilated balloon.
Figure 11B:
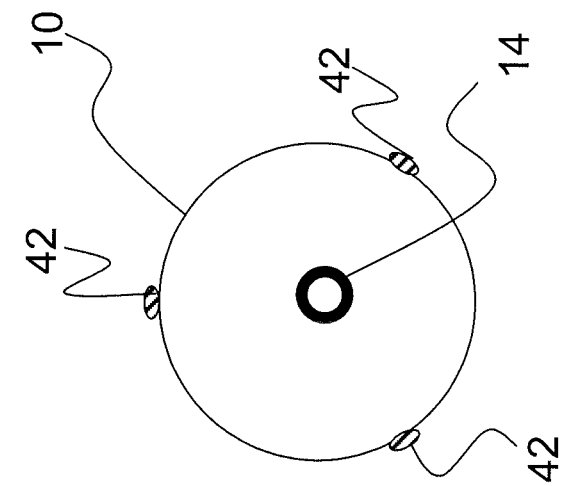
Figure 11A:
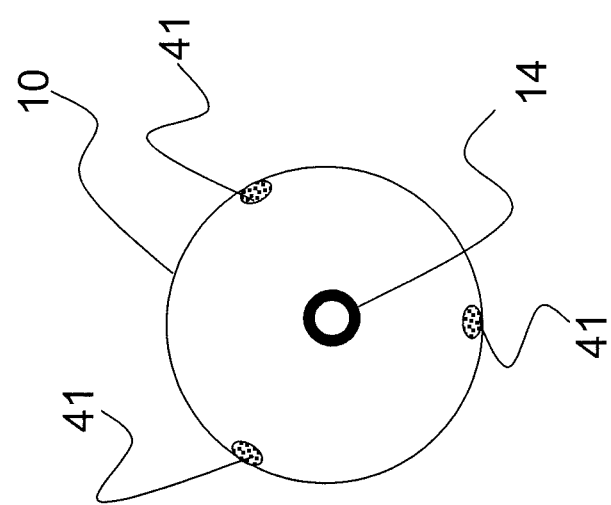
Figure 12C:
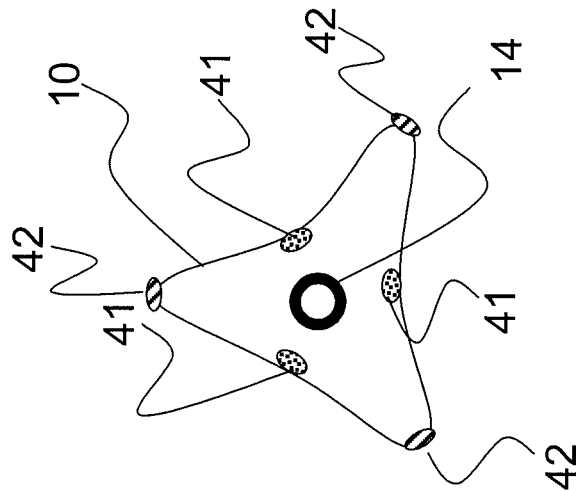
FIGS. 12a, b and c show cross-sectional views of the exemplary embodiments shown in FIGS. 11a, b and c in the partially deflated state.
Figure 12B:
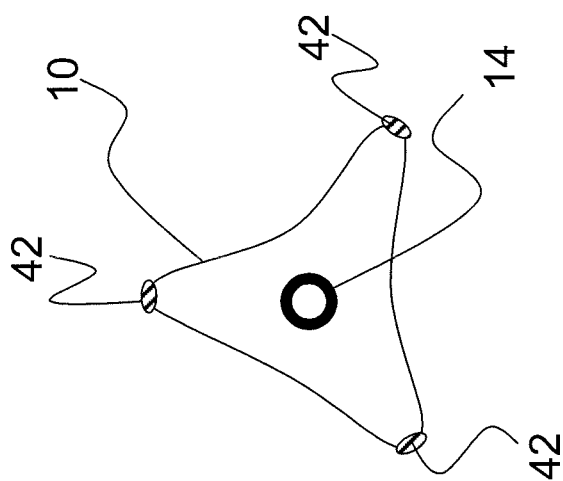
Figure 12A:
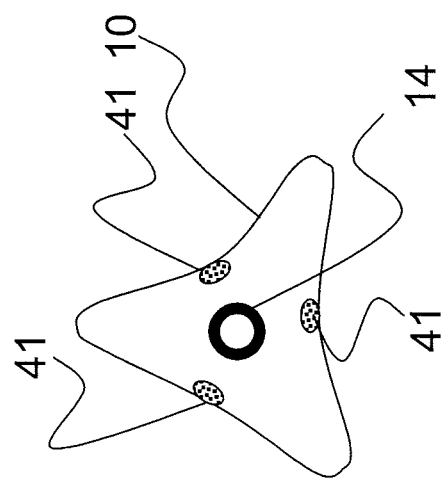
Figure 13C:
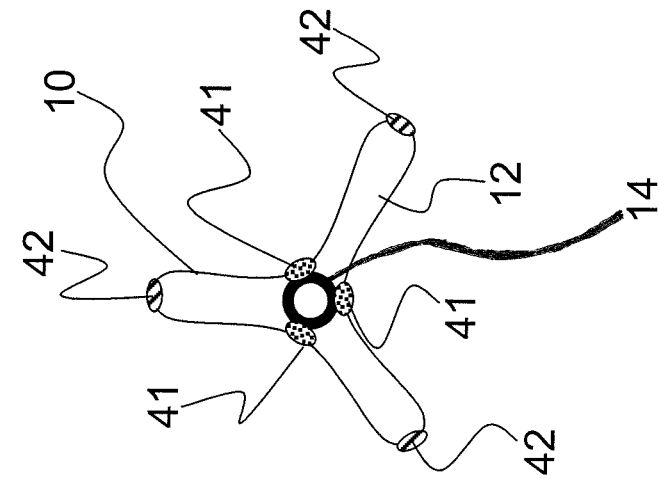
FIGS. 13a, b and c show cross-sectional views of the exemplary embodiments shown in FIGS. 11a, b and c in a further deflated state in comparison with FIGS. 9a, b and c.
Figure 13B:
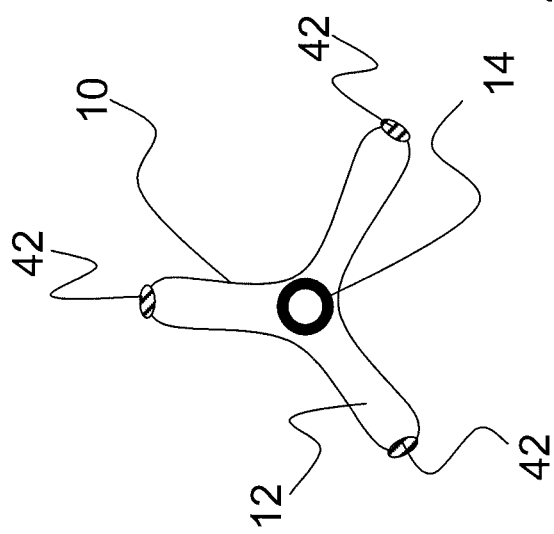
Figure 13A:
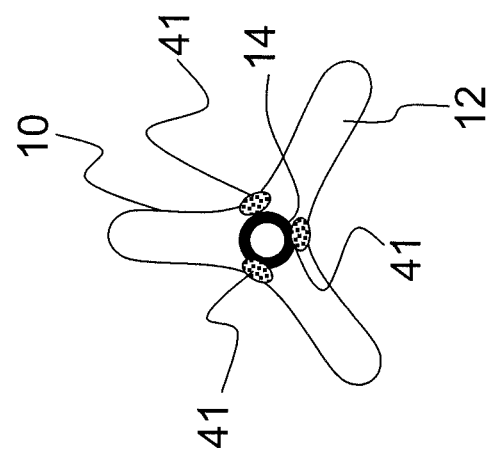

FIGS. 11, 12 and 13 show a balloon in which areas (webs) made of a material different from the balloon material act as fold elements. In FIGS. 11a, 12a and 13a, a balloon 10 of the material PEBAX is shown, having on the inside of the balloon surface webs 41 of the material PA12 running in the longitudinal direction of the balloon. On inflation, the PA12 webs 41 resist the internal pressure of the balloon to a greater extent and therefore store more elastic energy than the balloon wall made of PEBAX. In deflation, the resulting difference in shape is sufficient so that the webs 41 are arranged in the folds which form the transition between two wings 12.

In the exemplary embodiment shown in FIGS. 11b, 12b and 13b, the webs applied to the outside contract less on deflation than the surrounding balloon wall if the webs have stored less frozen-in tensile stress from the thermoforming process, for example. For example, PA12 is used as the balloon material while the webs 42, which are arranged on the outside of the balloon and run in the longitudinal direction of the catheter, are made of PEBAX. The fold elements 42 are arranged in the fold on the front end of the wings 12 on deflation because the fold elements 42 are under less tensile stress than the balloon wall.

FIGS. 11c, 12c and 13c show an exemplary embodiment which combines the exemplary embodiments shown in FIGS. 11a, 12a and 13a and/or 11b, 12b and 13b, using PEBAX as the balloon material. Web 42 here represents an area of increased wall thickness. Due to the smaller expansion of the outer membrane in comparison with the inner membrane in the thermoforming process, a web applied to the outside surface essentially has a lower stress immediately after forming than the inside membrane and/or the balloon membrane.

A catheter as disclosed in the present invention can be produced by the following method.

First, the balloon 10 is produced by blow molding, for example, where the blow mold has elevations where the fold lines 11 are to be provided, so that recesses are formed at the corresponding location in the balloon 10. Alternatively, a balloon 10 can be produced with webs by means of injection blow molding. Next, the balloon 10 with the fold lines 11, which preferably run at an angle α to the balloon axis A, is attached to the catheter base body, i.e., specifically to the inside shaft 14 and the outside shaft 15.

The exemplary embodiment shown in FIGS. 4-6 with a twisted balloon which has been permanently thermally fixed in its twisted state represents another exemplary embodiment for establishing a self-refolding balloon, i.e., a balloon that refolds itself in a defined manner with a uniform bending moment.

In another exemplary embodiment of the method of the present disclosure, the balloon may also be provided with fold lines subsequently, i.e., after being joined to the inside shaft and outside shaft, e.g., in the dilated state, by treating the balloon membrane locally by means of a laser, for example. The laser may be used so that the focus of the laser is guided along the fold lines 11 that are to be created, for example, and in this area the top layer of the balloon membrane is removed thermally. As an alternative, a solvent may be used to wet the areas along the fold lines 11 that are to be created and alter the structure of the balloon membrane there. In this way, the stiffness of the balloon membrane is altered in comparison with the surrounding area in the thermally altered area or the area treated by the solvent.

All patents, patent applications and publications referred to herein are incorporated by reference in their entirety.

What is claimed is:

1. A catheter, comprising: a balloon having a proximal end and a distal end and a dilated and an undilated state and having at least one wing in the undilated state, the balloon in the dilated state having a plurality of fold elements with at least one fold element running essentially in a longitudinal direction for each wing but at a fixedly defined non-zero angle ($\alpha$) to a longitudinal axis of the balloon along its length between areas of the distal and proximal ends, at least a portion of the fold element in the areas of the distal and proximal ends being at a nonparallel angle with respect to an adjacent fold element proximate either to one of or both the proximal and distal ends and remaining portions of the fold element along the length between areas of the distal and proximal ends being parallel to the adjacent fold element in the dilated state, wherein the fold element of the balloon is formed by a longitudinal strut which forms a structure that is arranged on either the inside, outside or both inside and outside of the balloon and supports the balloon at defined locations, the balloon made of a first polymer, the longitudinal strut made of a polymer different from the first polymer or a metal wire, such that when the balloon is folded, the fold element is arranged in an area of the wing running in the longitudinal direction with a minimum in the bending radius.

2. The catheter of claim 1, wherein the balloon has either recesses or elevations in a wall thickness in the area of the fold element.

3. The catheter of claim 1, wherein the catheter in the undilated state further comprises at least one active pharmaceutical substance comprising a composition selected from the group consisting of, taxols, taxans, paclitaxel, and sirolimus and, the at least one active pharmaceutical substance further comprising at least one hyperplastic active ingredient having a distribution coefficient between the distribution coefficients of butanol and water of $\geq 0.5$ and which is arranged at least partially beneath the at least one wing of the balloon in the undilated state.

4. The catheter of claim 1, wherein the longitudinal strut forms a spiral on the balloon.

5. The catheter of claim 1, wherein the longitudinal strut is a metal wire.

6. The catheter of claim 1, wherein the at least one fold element has interruptions along the longitudinal direction.

7. A system for introducing an intraluminal endoprothesis, such as a stent, into a body cavity, the system comprising:

a) an intraluminal endoprosthesis and
b) a catheter comprising a balloon having a proximal and a distal end and a dilated and an undilated state and having at least one wing in the undilated state, the balloon in the dilated state having a plurality of fold elements with at least one fold element running essentially in a longitudinal direction for each wing but at a fixedly defined non-zero angle ($\alpha$) to a longitudinal axis of the balloon along its length between areas of the distal and proximal ends in the dilated state, at least a portion of the fold element in the areas of the distal and proximal ends being at a nonparallel angle with respect to an adjacent fold element proximate either to one of or both the proximal and distal ends and remaining portions of the fold element along the length between areas of the distal and proximal ends being parallel to the adjacent fold element in the dilated state, wherein the fold element of the balloon is formed by a longitudinal strut which forms a structure that is arranged on either the inside, outside, or both inside and outside of the balloon and supports the balloon at defined locations, the balloon made of a first polymer, the longitudinal strut made of a polymer different from the first polymer or a metal wire, wherein the intraluminal endoprosthesis is fixedly arranged on the folded balloon such that the intraluminal endoprosthesis at least partially surrounds the folded balloon.

8. The system of claim 7, wherein the intraluminal endoprosthesis is a biodegradable stent.

9. The system of claim 7, wherein the lumen of the intraluminal endoprosthesis is coated with a removable material comprising one or more substances selected from the group consisting of sugars, polysaccharides, glycans, glucose, glycogen, amylose, amylopectin, chitin, callose and cellulose, and fats, cholesterin, cholesterol, palm oil, partially hydrogenated soy oils and saturated oils.

10. The system of claim 7, wherein the longitudinal strut forms a spiral on the balloon.

11. The system of claim 7, wherein the longitudinal strut is a metal wire.

12. The system of claim 7, wherein the balloon in the undilated state further comprises at least one active pharmaceutical substance comprising a composition selected from the group consisting of, taxols, taxans, paclitaxel, and sirolimus and, the at least one active pharmaceutical substance further comprising at least one hyperplastic active ingredient having a distribution coefficient between the distribution coefficients of butanol and water of $\geq 0.5$ and which is arranged at least partially beneath the at least one wing of the balloon in the undilated state.

13. The system of claim 7, wherein the at least one fold element has interruptions along the longitudinal direction.

14. A method for producing a catheter, comprising:

a) providing a balloon having a dilated and an undilated state and having at least one wing in the undilated state, the balloon in the dilated state having a plurality of fold elements with at least one fold element running essentially in the longitudinal direction for each wing, the balloon in the dilated state having a plurality of fold elements with at least one fold element running essentially in a longitudinal direction for each wing but at a fixedly defined non-zero angle ($\alpha$) to a longitudinal axis of the balloon along its length between areas of the distal and proximal ends, at least a portion of the fold element in the areas of the distal and proximal ends being at a nonparallel angle with respect to an adjacent fold element proximate either to one of or both the proximal and distal ends and remaining portions of the fold element along the length between areas of the distal and proximal ends being parallel to the adjacent fold element in the dilated state, wherein the fold element of the balloon is formed by a longitudinal strut which forms a structure that is arranged on either the inside, outside or both inside and outside of the balloon and supports the balloon at defined locations, the balloon made of a first polymer, the longitudinal strut made of a polymer different from the first polymer or a metal wire, such that when the balloon is folded, the fold element is arranged in an area of the wing running in the longitudinal direction with a minimum in the bending radius;

b) providing a catheter base body having an inside shaft and an outside shaft; and c) connecting the balloon to the inside shaft and the outside shaft.

15. The method of claim 14, wherein the balloon is produced by blow molding, whereby the blow mold is provided with either a recess or an elevation at the location where the at least one fold element is to be formed.

16. The method of claim 14, wherein the balloon is produced by injection blow molding such that at least one defined sudden change in wall thickness is created at the location where the at least one fold element is to be formed.

17. The method of claim 14, wherein the balloon is connected on either the inside, outside or both inside and outside to a structure comprising longitudinal struts, the structure supporting the balloon in certain areas.

18. The method of claim 14, wherein the balloon is thermally treated locally in the area of the at least one fold element before applying an active pharmaceutical substance to the surface of the balloon.

19. The method of claim 14, wherein the balloon is treated with a solvent in the area of the at least one fold element before applying an active pharmaceutical substance.

20. The method of claim 14, wherein the balloon further comprises a reinforcing material in the area outside of the at least one fold element.

21. The method of claim 14, wherein at least one active pharmaceutical substance is applied either onto or into the outer surface of the balloon before folding, said application being achieved by either dipping, spraying, painting or pressing, whereby the active pharmaceutical substance comprises either taxols or taxans, and further comprises at least one hyperplastic active ingredient having a distribution coefficient between the distribution coefficients of butanol and water of ≥0.5 in the undilated state.

22. The method of claim 21, further comprising the step of folding the balloon, wherein after the folding step, any excess at least one active pharmaceutical substance and any excess carrier material is substantially removed from the surfaces of the balloon that are on the outside after folding.

23. The method of claim 21, wherein the at least one active pharmaceutical substance is either cured or polymerized.

24. The method of claim 21, wherein the active pharmaceutical substance is applied to the balloon when the balloon is in the dilated state.

25. The method of claim 14, wherein the active pharmaceutical substance is embedded in a carrier for application to the balloon, the carrier comprising at least one material selected from the group comprising a contrast medium, an organic salt, and an inorganic salt, and the carrier further comprises at least one additional additive serving either to improve the mechanical adhesion to the balloon surface, to improve the release of the active pharmaceutical substance to the vascular wall, or to improve the uptake ability of the vascular wall.

26. The method of claim 14, wherein the balloon is connected to the inside shaft and the outside shaft and then the inside shaft and the outside shaft of the catheter are rotated or displaced before being joined together.

27. A method for producing a system for introducing an intraluminal endoprosthesis, such as a stent, into a body cavity, the method comprising:

a) providing an intraluminal endoprosthesis;
b) providing a catheter comprising
  (i) a balloon having a dilated and an undilated state and having at least one wing in the undilated state, the balloon in the dilated state having a plurality of fold elements with at least one fold element running essentially in the longitudinal direction for each wing, the balloon in the dilated state having a plurality of fold elements with at least one fold element running essentially in a longitudinal direction for each wing but at a fixedly defined non-zero angle ($\alpha$) to a longitudinal axis of the balloon along its length between areas of the distal and proximal ends, at least a portion of the fold element in the areas of the distal and proximal ends being at a nonparallel angle with respect to an adjacent fold element proximate either to one or both the proximal and distal ends and remaining portions of the fold element along the length between areas of the distal and proximal ends being parallel to the adjacent fold element in the dilated state, wherein the fold element of the balloon is formed by a longitudinal strut which forms a structure that is arranged on either the inside, outside or both inside and outside of the balloon and supports the balloon at defined locations, the balloon made of a first polymer, the longitudinal strut made of a polymer different from the first polymer or a metal wire, such that when the balloon is folded, the fold element is arranged in an area of the wing running in the longitudinal direction with a minimum in the bending radius, and
  (ii) a base body having an inside shaft and an outside shaft;
c) forming at least one wing on the balloon;
d) folding the balloon;
e) bringing the at least one wing into close contact with the inside shaft; and,
f) fixedly associating the intraluminal endoprosthesis on the folded balloon such that the intraluminal endoprosthesis at least partially surrounds the folded balloon.

28. The method of claim 27, wherein the intraluminal endoprosthesis is associated on the balloon by means of crimping.

29. The method of claim 27, wherein the balloon has a distal end and a proximal end, the method further comprising the step of applying at least one active pharmaceutical substance to at least a portion of the balloon, the portion substantially excluding the distal and proximal ends.

30. The method of claim 27, after d) and before e) further comprising applying an easily washed off coating to at least a portion of the luminal surface of the intraluminal endoprosthesis, the coating comprising one or more substances selected from the group consisting of (a) one or more sugars selected from the group consisting of polysaccharides, glycans, glucose, glycogen, amylose, amylopectin, chitin, callose, cellulose, and (b) one or more fats selected from the group consisting of cholesterin, cholesterol, palm oil, partially hydrogenated soy oils and saturated oils.

31. A balloon for use in a catheter, the balloon having a proximal end and a distal end and a dilated and an undilated state and comprising: at least one wing in the undilated state, the balloon in the dilated state having a plurality of fold elements with at least one fold element running essentially in the longitudinal direction for each wing but at a fixedly defined non-zero angle (α) to a longitudinal axis of the balloon along its length between areas of the distal and proximal ends, at least a portion of the fold element in the areas of the distal and proximal ends being at a non-parallel angle with respect to an adjacent fold element proximate either to one of or both the proximal and distal ends and remaining portions of the fold element along the length between areas of the distal and proximal ends being parallel to the adjacent fold element in the dilated state, wherein the fold element of the balloon is formed by a longitudinal strut which forms a structure that is arranged on either the inside, outside or both inside and outside of the balloon and supports the balloon at defined locations, the balloon made of a first polymer, the longitudinal struts made of a polymer different from the first polymer or a metal wire, such that when the balloon is folded the fold element is arranged in an area of the wing running in the longitudinal direction with a minimum in the bending radius.

32. The balloon of claim 31, wherein the longitudinal strut forms a spiral on the balloon.

33. The balloon of claim 31, wherein the longitudinal strut is a metal wire.

34. The balloon of claim 31, wherein the balloon in the undilated state further comprises at least one active pharmaceutical substance comprising a composition selected from the group consisting of, taxols, taxans, paclitaxel, and sirolimus and, the at least one active pharmaceutical substance further comprising at least one hyperplastic active ingredient having a distribution coefficient between the distribution coefficients of butanol and water of ≥0.5 and which is arranged at least partially beneath the at least one wing of the balloon in the undilated state.

35. The balloon of claim 31, wherein the at least one fold element has interruptions along the longitudinal direction.

* * * * *